US012746246B2

(12) United States Patent
Yates et al.

(10) Patent No.: US 12,746,246 B2
(45) Date of Patent: Sep. 29, 2026

(54) COMPOSITIONS AND METHODS FOR TREATING AGE-RELATED MACULAR DEGENERATION

(71) Applicant: University of Virginia Patent Foundation, Charlottesville, VA (US)

(72) Inventors: Paul Andrew Yates, Charlottesville, VA (US); Elias Reichel, Weston, MA (US); Ashton Leone, Charlottesville, VA (US)

(73) Assignees: University of Virginia Patent Foundation, Charlottesville, VA (US); Tufts Medical Center, Inc., Boston, MA (US)

( * ) Notice: Subject to any disclaimer, the term of this patent is extended or adjusted under 35 U.S.C. 154(b) by 1227 days.

(21) Appl. No.: 17/598,660

(22) PCT Filed: Mar. 27, 2020

(86) PCT No.: PCT/US2020/025354
§ 371 (c)(1),
(2) Date: Sep. 27, 2021

(87) PCT Pub. No.: WO2020/198634
PCT Pub. Date: Oct. 1, 2020

(65) Prior Publication Data

US 2022/0184102 A1 Jun. 16, 2022

Related U.S. Application Data

(60) Provisional application No. 62/824,694, filed on Mar. 27, 2019.

(51) Int. Cl.
*A61K 31/65* (2006.01)
*A61P 27/02* (2006.01)

(52) U.S. Cl.
CPC .............. *A61K 31/65* (2013.01); *A61P 27/02* (2018.01)

(58) Field of Classification Search
None
See application file for complete search history.

(56) References Cited

U.S. PATENT DOCUMENTS

2005/0245497 A1 11/2005 Penfold et al.
2005/0256081 A1 11/2005 Peyman
2009/0136514 A1 5/2009 Power
2012/0028929 A1* 2/2012 Power ..................... A61P 29/00 514/153
2012/0202885 A1 8/2012 Widder et al.

OTHER PUBLICATIONS

Leung et al., Expert Review of Clinical Pharmacology, 2013, 6(5), 565-579.*
Alikhan et al., "The role of tetracyclines in rosacea." Am. J. Clin. Dermatol., vol. 11(2), pp. 79-87 (2010).
Anderson et al., "Characterization of beta amyloid assemblies in drusen: the deposits associated with aging and age-related macular degeneration." Exp. Eye Res., vol. 78(2), pp. 243-256 (2004).
Antoniak et al., "Age-related macular degeneration—a complex genetic disease." Klin Oczna, vol. 110(4-6), pp. 211-218 (2008).
Brown et al., "Age-related macular degeneration: economic burden and value-based medicine analysis." Can. J. Ophthalmol., vol. 40(3), pp. 277-287 (2005).
Ciancio, "Safety and efficacy of sub-antimicrobial-dose doxycycline therapy in patients with adult periodontitis." Adv. Dent. Res., vol. 12(2), pp. 27-31 (1998).
Cox et al., "Doxycycline's effect on ocular angiogenesis: an in vivo analysis." Ophthalmology, vol. 117(9), pp. 1782-1791 (2010).
Cukras et al., "Oral minocycline for the treatment of diabetic macular edema (DME): results of a phase I/II clinical study." Invest. Ophthalmol. Vis. Sci., vol. 53(7), pp. 3865-3874 (2012).
Del Rosso et al., "Two randomized phase III clinical trials evaluating anti-inflammatory dose doxycycline (40-mg doxycycline, USP capsules) administered once daily for treatment of rosacea." J. Am. Acad. Dermatol., vol. 56(5), pp. 791-802 (2007).
Donoso et al., "The role of complement Factor H in age-related macular degeneration: a review." Surv. Ophthalmol., vol. 55(3), pp. 227-246 (2010).
Gehrs et al., "Age-related macular degeneration—emerging pathogenetic and therapeutic concepts." Ann. Med., vol. 38(7), pp. 450-471 (2006).
International Preliminary Report on Patentability Corresponding to International Application No. PCT/US 2020/025354 dated Oct. 7, 2021.

(Continued)

*Primary Examiner* — Sun Jae Yoo
(74) *Attorney, Agent, or Firm* — Jenkins, Taylor & Hunt, P.A.

(57) ABSTRACT

Provided are chemically modified tetracycline (CMT) derivatives for the treatment of non-exudative macular degeneration. The CMT derivatives lack antimicrobial activity, include a phenol ring, and a chemical structure sufficient to chelate Zn2+. Methods of inhibiting and/or minimizing inflammation in a subject, including administering to the subject a dose of a CMT derivative, are also provided. Methods of treating non-exudative age-related macular degeneration (AMD) are provided.

7 Claims, 6 Drawing Sheets

(56) References Cited

OTHER PUBLICATIONS

International Search Report and the Written Opinion of the International Searching Authority Corresponding to International Application No. PCT/US 2020/025354 dated Jun. 19, 2020.
Kircik, "Doxycycline and minocycline for the management of acne: a review of efficacy and safety with emphasis on clinical implications." J. Drugs Dermatol., vol. 9(11), pp. 1407-1411 (2010).
Leung et al., "Minocycline protects photoreceptors from light and oxidative stress in primary bovine retinal cell culture." Invest. Ophthalmol. Vis. Sci., vol. 48(1), pp. 412-421 (2007).
Lindeman et al., "Clinical trial of doxycycline for matrix metalloproteinase-9 inhibition in patients with an abdominal aneurysm: doxycycline selectively depletes aortic wall neutrophils and cytotoxic T cells." Circulation, vol. 119(16), pp. 2209-2216 (2009).
Liu and Khalil, "Tetracycline-Based MMP Inhibitors," Matrix Metalloproteinases and Tissue Remodeling in Health and Disease: Target Tissues and Therapy, Academic Press (2017).
McGuinness et al., "Cochrane review on 'Statins for the treatment of dementia'." Int. J. Geriatr. Psychiatry, vol. 28(2), pp. 119-126 (2013).
Molloy et al., "A multicenter, blinded, randomized, factorial controlled trial of doxycycline and rifampin for treatment of Alzheimer's disease: the DARAD trial." Int. J. Geriatr. Psychiatry, vol. 28(5), pp. 463-470 (2013).
O'Dell et al., "Treatment of early seropositive rheumatoid arthritis: doxycycline plus methotrexate versus methotrexate alone." Arthritis Rheum., vol. 54(2), pp. 621-627 (2006).
Payne et al., "The effect of subantimicrobial-dose-doxycycline periodontal therapy on serum biomarkers of systemic inflammation: a randomized, double-masked, placebo-controlled clinical trial." J. Am. Dent. Assoc., vol. 142(3), pp. 262-273 (2011).
Preshaw et al., "Modified-release subantimicrobial dose doxycycline enhances scaling and root planing in subjects with periodontal disease." J. Periodontol., vol. 79(3), pp. 440-452 (2008).
Ramrattan et al., "Morphometric analysis of Bruch's membrane, the choriocapillaris, and the choroid in aging." Invest. Ophthalmol. Vis. Sci., vol. 35(6), pp. 2857-2864 (1994).
Rinninella et al., "The Role of Diet, Micronutrients, and the Gut Microbiota in Age-Related Macular Degeneration: New Perspectives from the Gut(-)Retina Axis." Nutrients, vol. 10(11) (26 pages) (2018).
Scholz et al., "Minocycline counter-regulates pro-inflammatory microglia responses in the retina and protects from degeneration." J. Neuroinflammation, vol. 12, p. 209 (2015).
Scott et al., "Effect of doxycycline vs placebo on retinal function and diabetic retinopathy progression in mild to moderate nonproliferative diabetic retinopathy: a randomized proof-of-concept clinical trial." JAMA Ophthalmol., vol. 132(9), pp. 1137-1142 (2014).
Sivaprasad et al., "A pilot study on the combination treatment of reduced-fluence photodynamic therapy, intravitreal ranibizumab, intravitreal dexamethasone and oral minocycline for neovascular age-related macular degeneration." Ophthalmologica, vol. 225(4), pp. 200-206 (2011).
Soliman et al., "Minocycline block copolymer micelles and their anti-inflammatory effects on microglia." Macromol. Biosci., vol. 10(3), pp. 278-288 (2010).
Walker et al., "Long-term treatment with sub-antimicrobial dose doxycycline has no antibacterial effect on intestinal flora." J. Clin. Periodontol., vol. 32, pp. 1163-1169 (2005).
WHO, "Blindness and vision impairment" fact sheet; Available from: http://www.who.int/mediacentre/factsheets/fs282/en/.
Wikipedia, "Tetracycline antibiotics," Oct. 6, 2018, retrieved on Jun. 4, 2020 from https://en.wikipedia.org/w/index.php?title=Tetracycline_antibiotics&oldid=862774706.
Wirostko et al., "Age related macular degeneration is an inflammatory disease possibly treatable with minocycline." Acta Ophthalmol., vol. 82(2), pp. 243-244 (2004).
Zhao et al., "Minocycline attenuates photoreceptor degeneration in a mouse model of subretinal hemorrhage microglial: inhibition as a potential therapeutic strategy." Am. J. Pathol., vol. 179(3), pp. 1265-1277 (2011).

* cited by examiner

TETRACYCLINE

DOXYCYCLINE

MINOCYCLINE

COMPOSITIONS AND METHODS FOR TREATING AGE-RELATED MACULAR DEGENERATION

CROSS-REFERENCE TO RELATED APPLICATIONS

This application is a national phase application of PCT International Patent Application PCT/US2020/025354, filed Mar. 27, 2020, herein incorporated by reference in its entirety and which claims benefit of U.S. Provisional Application Ser. No. 62/824,694, filed Mar. 27, 2019, herein incorporated by reference in its entirety.

TECHNICAL FIELD

The presently disclosed subject matter is directed to compositions and methods for treating age-related macular degeneration.

BACKGROUND

Age-related macular degeneration (AMD) is the leading cause of blindness and visual disability in adults over age 60 in the United States. 20% of the United States population aged 65-74 years and 35% of people aged 75 years or more have the disease[1]. AMD is divided into "wet" (exudative or neovascular) and "dry" (non-exudative or atrophic) disease. In the United States alone, 1.6 million new cases of dry AMD and over 150,000 new cases of wet AMD are diagnosed annually[1].

Dry AMD results from the loss and/or dysfunction of retinal pigment epithelial (RPE) cells in the macula, which are critical to the survival of retinal photoreceptors responsible for vision. The loss of RPE cells and subsequent photoreceptors leads to decreased light sensitivity, retinal thinning, and eventual loss of vision. The cause of the breakdown of the RPE layer and loss of photoreceptors remains unclear, but recent evidence suggests inflammation, oxidative stress, as well as other genetic and environmental factors play a critical role[4].

A key pathologic event in development of atrophic AMD is thought to be the accumulation of drusen between the RPE cells and the underlying Bruch's membrane that separates the RPE from the choroid[5]. The risk of vision loss directly correlates with both the number and size of drusen[6]. Drusen may directly or indirectly lead to loss of RPE cells and photoreceptors. Drusen result in retinal thinning and loss of the protective barrier between the RPE and underlying Bruch's membrane[7]. This loss of integrity allows for formation of sub-retinal neovascularization leading to development of wet AMD. Anti-vascular endothelial growth factor (VEGF) therapies are effective in treating the 10% of patients with the neovascular form of AMD[8]. However, there is no treatment or preventative therapy available for the remaining 90% of dry AMD patients[9].

What is needed are new therapeutic agents, compositions and methos for treating AMD and related conditions.

SUMMARY

This summary lists several embodiments of the presently disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this summary or not. To avoid excessive repetition, this Summary does not list or suggest all possible combinations of such features.

In some embodiments, provided herein are chemically modified tetracycline (CMT) derivatives for the treatment of non-exudative macular degeneration. In some aspects, such CMT derivatives lack anti-microbial activity, comprise a phenol ring, and comprise a chemical structure sufficient to chelate Zn2+. The CMT derivatives can lack antimicrobial activity due to deletion of a C4 dimethylamino. The CMT derivatives can lack antimicrobial activity due to dosing below a minimum inhibitory concentration. In some aspects, in the CMT derivatives the phenol ring can comprise a diethylamino group to enhance scavenging of reactive oxygen species. In some embodiments the chemical structure comprises the following structure:

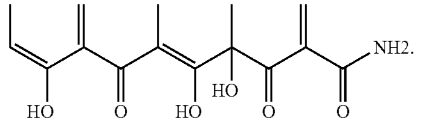 [SMILES: C=C(C(N)=O)C(=O)C(C)(O)/C(O)=C(\C)C(=O)C(=C)/C(O)=C\C]

In some embodiments, the disclosed CMT derivatives can comprise doxycycline. In some embodiments, the CMT derivative is given at a dose of 40 mg per day. In some embodiments, the CMT derivative is ORACEA® tetracycline derivative. In some embodiments, the dose of the doxycycline is given at a concentration less than 100 mg per day.

Also provided herein are methods of inhibiting and/or minimizing inflammation in a subject, the methods comprising administering to a subject in need a dose of a CMT derivative, wherein the dose of the CMT derivative is sufficient to inhibit activation of gut microbiome inflammatory cells, wherein the dose of the CMT derivative is below a minimum inhibitory concentration for antimicrobial activity. In some embodiments, the CMT derivative is administered at a dose of about 100 mg per day, optionally at a dose of about 40 mg per day. In some embodiments, the subject is a human subject, optionally wherein the human subject is suffering from non-exudative age-related macular degeneration.

In some aspects, provided herein are methods of treating non-exudative age-related macular degeneration (AMD) in a subject, the methods comprising providing a subject susceptible to and/or suffering from non-exudative AMD, and administering to the subject a CMT derivative as disclosed herein. In some embodiments, the CMT derivative is administered at a dose of about 100 mg per day, optionally at a dose of about 40 mg per day, optionally at a dose of less than about 40 mg per day. In some embodiments, the dose of the CMT derivative is sufficient to inhibit activation of gut microbiome inflammatory cells. In some embodiments, the dose of the CMT derivative is sufficient to decrease gut leakage of inflammatory cytokines. In some embodiments, the dose of the CMT derivative is below a minimum inhibitory concentration for antimicrobial activity. In some embodiments, the dose of the CMT derivative is sufficient to prevent activation of inflammatory cells that can transit to a retina of the subject. In some embodiments, the dose of the CMT derivative is sufficient to inhibit pro-inflammatory pathways to an eye of the subject.

In some embodiments, provided herein are compositions for administration to a subject, the compositions comprising a chemically modified tetracycline (CMT) derivative, wherein the CMT derivative lacks anti-microbial activity, comprises a phenol ring, and comprises a chemical structure sufficient to chelate $Zn^{2+}$, and wherein the CMT derivative is included in the composition at a concentration sufficient to provide a dose of about 40 mg per day when administered to a subject. In some embodiments, the composition is configured to treatment non-exudative macular degeneration when administered to a subject. In some embodiments, the CMT derivative lacks antimicrobial activity due to deletion of a C4 dimethylamino. In some embodiments, the CMT derivative lacks antimicrobial activity due to dosing below a minimum inhibitory concentration. In some embodiments, the CMT derivative is doxycycline. In some embodiments, the compostions further comprise an excipient or a pharmaceutically acceptable carrier.

Accordingly, it is an object of the presently disclosed subject matter to provide compositions and methods for treating age-related macular degeneration. This and other objects are achieved in whole or in part by the presently disclosed subject matter. Further, an object of the presently disclosed subject matter having been stated above, other objects and advantages of the presently disclosed subject matter will become apparent to those skilled in the art after a study of the following description, Drawings and Examples.

BRIEF DESCRIPTION OF THE DRAWINGS

The presently disclosed subject matter can be better understood by referring to the following figures. The components in the figures are not necessarily to scale, emphasis instead being placed upon illustrating the principles of the presently disclosed subject matter (often schematically). In the figures, like reference numerals designate corresponding parts throughout the different views. A further understanding of the presently disclosed subject matter can be obtained by reference to an embodiment set forth in the illustrations of the accompanying drawings. Although the illustrated embodiment is merely exemplary of systems for carrying out the presently disclosed subject matter, both the organization and method of operation of the presently disclosed subject matter, in general, together with further objectives and advantages thereof, may be more easily understood by reference to the drawings and the following description. The drawings are not intended to limit the scope of this presently disclosed subject matter, which is set forth with particularity in the claims as appended or as subsequently amended, but merely to clarify and exemplify the presently disclosed subject matter.

For a more complete understanding of the presently disclosed subject matter, reference is now made to the following drawings in which:

FIGS. 5A-5B, Patient 1; FIGS. 5C-5D, Patient 2; FIGS. 5E-5F, Patient 3; FIGS. 5G-5H, Patient 4.

DETAILED DESCRIPTION

The presently disclosed subject matter now will be described more fully hereinafter, in which some, but not all embodiments of the presently disclosed subject matter are described. Indeed, the presently disclosed subject matter can be embodied in many different forms and should not be construed as limited to the embodiments set forth herein; rather, these embodiments are provided so that this disclosure will satisfy applicable legal requirements.

I. General Considerations

Figure 3:
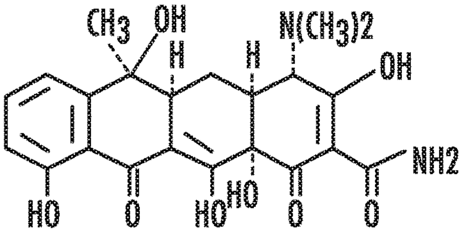
FIG. 3 shows the chemical structures of tetracyclines.
Figure 3:
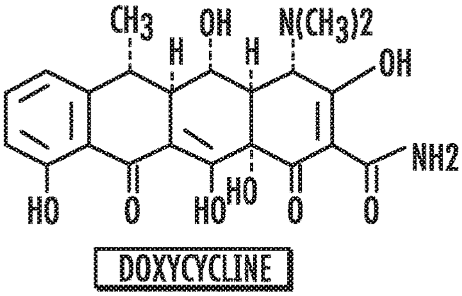
Figure 3:
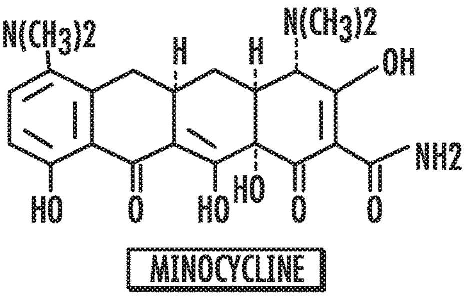

In some embodiments, provided herein are a chemically modified tetracycline (CMT) derivatives, including those for the treatment of non-exudative macular degeneration. The CMT derivatives can be configured to lack anti-microbial activity, comprise a phenol ring, and/or comprise a chemical structure sufficient to chelate Zn2+. The CMT derivatives can lack antimicrobial activity due to deletion of a C4 dimethylamino, and/or due to dosing below a minimum inhibitory concentration. The structures of the CMT derivatives can be based on the structures shown in FIG. 3, and derivatives thereof. As discussed further herein, in some aspects the chemical structure comprises the following structure:

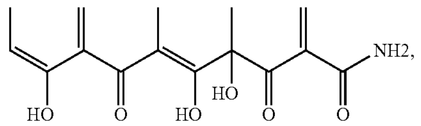 [SMILES: C=C(C(N)=O)C(=O)C(C)(O)/C(O)=C(\C)C(=O)C(=C)/C(O)=C\C]

also referred to the bottom half of a tetracycline compound. In some aspects, the CMT derivative is doxycycline.

Correspondingly, provided herein are compositions for administration to a subject, the compositions comprising a chemically modified tetracycline (CMT) derivative, and optionally an excipient or other pharmaceutically acceptable carrier. As discussed further herein, such compositions can include one or more desirable properties, including for example a lack of anti-microbial activity, a phenol ring, and/or a chemical structure sufficient to chelate Zn2+. Notably, the CMT derivative can be included in the composition at a concentration sufficient to provide a dose of about 40 mg per day when administered to a subject, optionally less than about 100 mg per day, less than about 80 mg per day, less than about 60 mg per day, less than about 50 mg per day, less than about 45 mg per day, or less than about 35 mg per day. Such compositions can be configured to treat non-exudative macular degeneration when administered to a subject.

As discussed further hereinbelow, methods of inhibiting and/or minimizing inflammation in a subject are provided. Correspondingly, methods of treating non-exudative age-related macular degeneration (AMD) in a subject are also provided. Such methods can include administering to a subject in need a CMT derivative as disclosed herein. The dose of the CMT derivative can be sufficient to inhibit activation of gut microbiome inflammatory cells, and/or below a minimum inhibitory concentration for antimicrobial activity, including the dosage concentrations and ranges discussed herein.

II. Definitions

While the following terms are believed to be well understood by one of ordinary skill in the art, the following definitions are set forth to facilitate explanation of the presently disclosed subject matter.

All technical and scientific terms used herein, unless otherwise defined below, are intended to have the same meaning as commonly understood by one of ordinary skill in the art. Mention of techniques employed herein are intended to refer to the techniques as commonly understood in the art, including variations on those techniques or substitutions of equivalent techniques that would be apparent to one of skill in the art. Thus, unless defined otherwise, all technical and scientific terms and any acronyms used herein have the same meanings as commonly understood by one of ordinary skill in the art in the field of the presently disclosed subject matter. Although any compositions, methods, kits, and means for communicating information similar or equivalent to those described herein can be used to practice the presently disclosed subject matter, particular compositions, methods, kits, and means for communicating information are described herein. It is understood that the particular compositions, methods, kits, and means for communicating information described herein are exemplary only and the presently disclosed subject matter is not intended to be limited to just those embodiments.

Following long-standing patent law convention, the terms "a", "an", and "the" refer to "one or more" when used in this application, including the claims. Thus, in some embodiments the phrase "a peptide" refers to one or more peptides.

The term "about", as used herein to refer to a measurable value such as an amount of weight, time, dose (e.g., therapeutic dose), etc., is meant to encompass in some embodiments variations of ±20%, in some embodiments ±10%, in some embodiments ±5%, in some embodiments ±1%, in some embodiments ±0.5%, in some embodiments ±0.1%, and in some embodiments ±0.01% from the specified amount, as such variations are appropriate to perform the disclosed methods.

As used herein, the term "and/or" when used in the context of a list of entities, refers to the entities being present singly or in any and every possible combination and subcombination. Thus, for example, the phrase "A, B, C, and/or D" includes A, B, C, and D individually, but also includes any and all combinations and subcombinations of A, B, C, and D. It is further understood that for each instance wherein multiple possible options are listed for a given element (i.e., for all "Markush Groups" and similar listings of optional components for any element), in some embodiments the optional components can be present singly or in any combination or subcombination of the optional components. It is implicit in these forms of lists that each and every combination and subcombination is envisioned and that each such combination or subcombination has not been listed simply merely for convenience. Additionally, it is further understood that all recitations of "or" are to be interpreted as "and/or" unless the context clearly requires that listed components be considered only in the alternative (e.g., if the components would be mutually exclusive in a given context and/or could not be employed in combination with each other).

As used herein, the term "subject" refers to an individual (e.g., human, animal, or other organism) to be assessed, evaluated, and/or treated by the methods or compositions of the presently disclosed subject matter. Subjects include, but are not limited to, mammals (e.g., murines, simians, equines, bovines, porcines, canines, felines, and the like), and includes humans. As used herein, the terms "subject" and "patient" are used interchangeably, unless otherwise noted.

As used herein, the terms "effective amount" and "therapeutically effective amount" are used interchangeably and refer to the amount that provides a therapeutic effect, e.g., an amount of a composition that is effective to treat or prevent pathological conditions in a subject.

As used herein, the term "adjuvant" as used herein refers to an agent which enhances the pharmaceutical effect of another agent.

A "compound", as used herein, refers to any type of substance or agent that is commonly considered a chemical, drug, or a candidate for use as a drug, as well as combinations and mixtures of the above. The term compound further encompasses molecules such as peptides and nucleic acids.

As used herein, a "derivative" of a compound refers to a chemical compound that can be produced from another compound of similar structure in one or more steps, such as in replacement of H by an alkyl, acyl, or amino group.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

The term "modulate", as used herein, refers to changing the level of an activity, function, or process. The term "modulate" encompasses both inhibiting and stimulating an activity, function, or process.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in an animal. In some embodiments, a pharmaceutically acceptable carrier is pharmaceutically acceptable for use in a human.

The term "standard", as used herein, refers to something used for comparison. For example, it can be a known standard agent or compound which is administered or added to a control sample and used for comparing results when measuring said compound in a test sample. Standard can also refer to an "internal standard", such as an agent or compound which is added at known amounts to a sample and is useful in determining such things as purification or recovery rates when a sample is processed or subjected to purification or extraction procedures before a marker of interest is measured.

The term "symptom", as used herein, refers to any morbid phenomenon or departure from the normal in structure, function, or sensation, experienced by the patient and indicative of disease. In contrast, a sign is objective evidence of disease. For example, a bloody nose is a sign. It is evident to the patient, doctor, nurse and other observers.

As used herein, the term "treating" includes prophylaxis of the specific disorder or condition, or alleviation of the symptoms associated with a specific disorder or condition and/or preventing or eliminating said symptoms. A "prophylactic" treatment is a treatment administered to a subject who does not exhibit signs of a disease or exhibits only early signs of the disease for the purpose of decreasing the risk of developing pathology associated with the disease.

A "therapeutic" treatment is a treatment administered to a subject who exhibits signs of pathology for the purpose of diminishing or eliminating those signs.

III. Compositions and Methods for Treating AMD

Several factors are now considered important in the initiation and progression of atrophic AMD, including chronic inflammation via complement pathway and macrophage and microglia activation, oxidative stress, programmed cell death, as well as genetic and environmental susceptibility[10]. Tetracycline derivatives are a therapy candidate for atrophic AMD, given their demonstrated ability to target many of these identified pathways that may contribute to the disease[8,11,12]. In particular, tetracyclines are known to reduce reactive oxygen species, inhibit matrix metalloproteinase's (MMPs) that are involved in the breakdown of the barrier between the RPE and Bruch's membrane, inhibit caspase activation and thereby prevent cell death, prevent complement activation, and inhibit cytokine production through their effects on microglia and T-cell activation[12].

Figure 1:
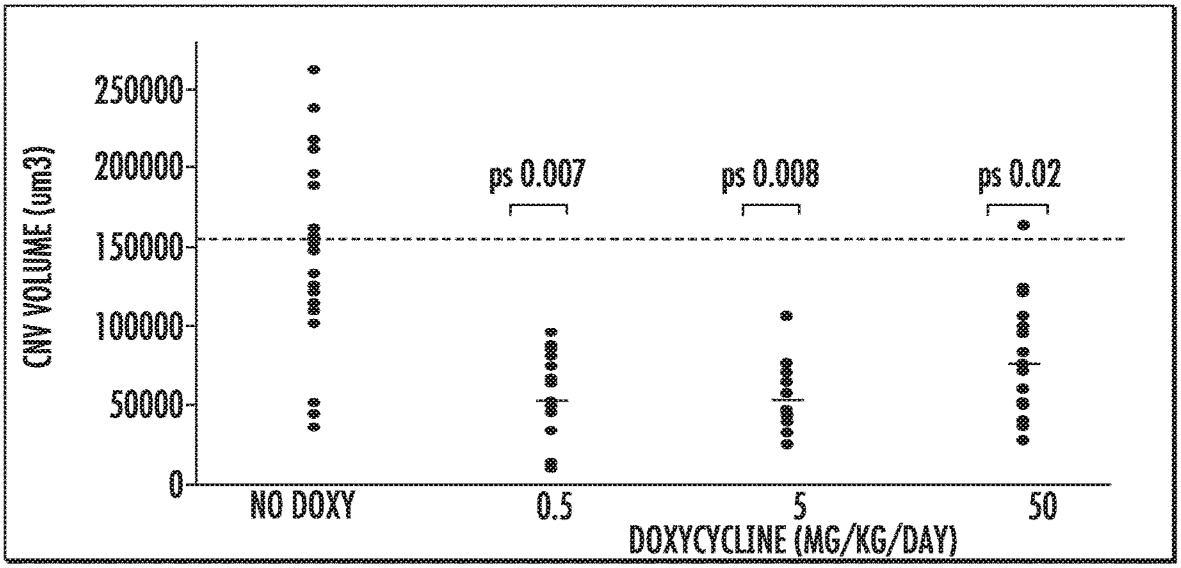
FIG. 1 is a plot of data showing that oral doxycycline inhibits volume of acute laser induced choroidal neo-vascularization in murine model of exudative AMD at all doses.

Following laser induced choroidal neovascularization (CNV), a model for exudative AMD, mice were fed 0.5 to 50 mg/kg of oral doxycycline in their water. Doxycycline treated mice demonstrated a >50% reduction in the volume of laser induced CNV compared to controls (FIG. 1)[13]. Minocycline was also found to attenuate photoreceptor degeneration in a mouse model of hemorrhagic neovascular AMD[14]. This effect was thought to be due to a decrease in microglial expression of chemotactic cytokines with a corresponding reduction of subretinal microglial infiltration[14]. Finally, minocycline has been shown to prevent retinal degeneration following light damage to the retina in a murine model of disease.[15] In vitro, human RPE cells were protected by minocycline against oxidative damage from both light exposure and oxidative stress[16]. However, the applicability of these findings to human disease, and specifically non-exudative AMD thus far remains unknown. These experiments involve acute insults in animal models and in vitro systems of retinal disease that very likely do not recapitulate the chronic degenerative aspects of non-exudate AMD, which involves decades long accumulation of drusen with progressive retinal dysfunction and degeneration.

There is very limited human data on the potential benefits of tetracycline derivatives. In a pilot study 18 patients were treated with reduced-fluence photodynamic therapy (PDT), intravitreal ranibizumab, intravitreal dexamethasone, and oral minocycline to treat neovascular exudative AMD". No safety concerns were identified during the course of the study, and stable vision was maintained in 89% of eyes. Outcomes with reduced-fluence PDT combination therapy were found to be equivalent to prior studies that examined combination therapy that used standard dose PDT with intravitreal ranibizumab alone. A clear synergistic benefit for the addition of oral minocycline to these established treatments for exudative AMD was unfortunately not established. A small phase I/II study using oral minocycline for treatment of diabetic macular edema demonstrated a possible effect in reduction of central macular thickness, but surprisingly these were not correlated with expected changes in systemic factors resulting from the known anti-inflammatory properties of minocycline. This discrepancy was attributed to the potential direct effects of microglial inhibition by minocycline in the retina.[18]

Figure 2:
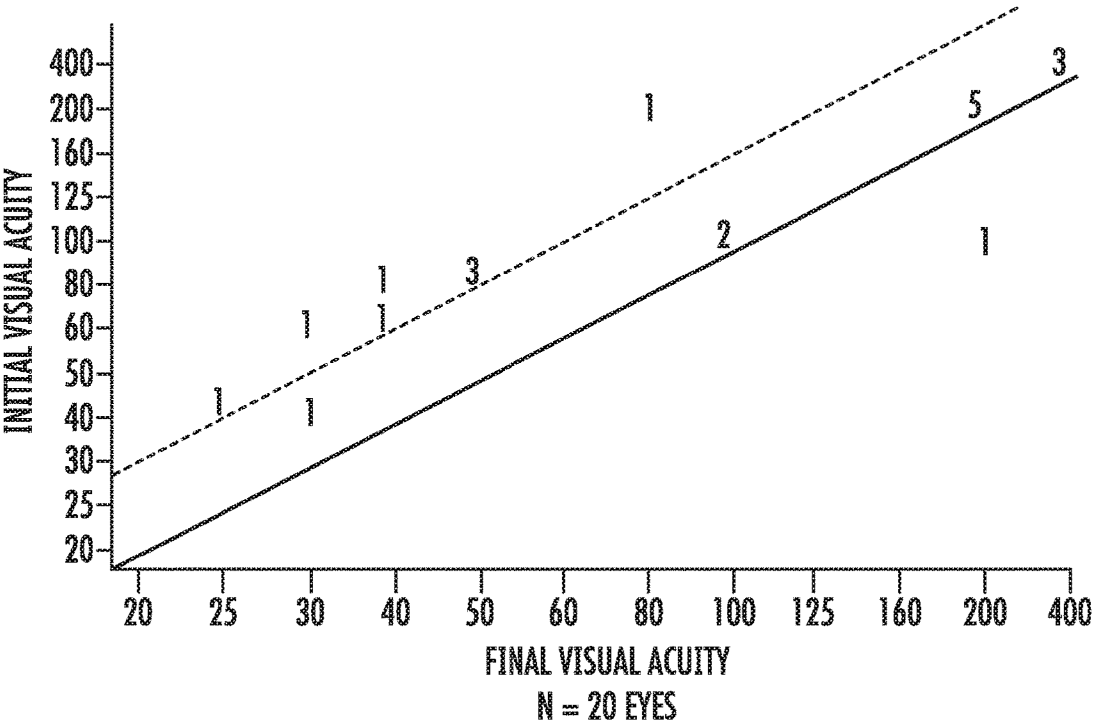
FIG. 2 is a graphical depiction of data showing the anecdotal improvement in visual acuity of 10 patients with stage 3 or 4 non-exudative AMD following treatment with tetracycline or minocycline.

A retrospective analysis of 10 patients with stage 3 or stage 4 non-exudative dry AMD[2,3] that were receiving treatment with tetracycline or minocycline for rheumatoid arthritis, dermatitis without keratitis, and acne rosacea demonstrated improvement of visual acuity over their one year course of treatment (FIG. 2). However, visual acuity is not an accepted metric for measuring the progression of non-exudative AMD. This anecdotal data included no measurement of the rate of increase in the area of geographic atrophy associated with non-exudative AMD, which is currently the gold standard for demonstrating pharmacologic efficacy for this disease. No retinal examination was indicated in these patients. In prior studies of potential therapeutics for non-exudative AMD, loss of visual acuity had only weak correlation with progression of disease, due to the fact that growth in geographic atrophy usually occurs well outside the fovea in most patients, before eventually involving the fovea. Further, doxycycline is currently a standard treatment for ocular rosacea and blepharitis. It is impossible to disassociate the potential effects on improvement in patient's possible, and very common, dry eye disease with taking tetracyclines from any effect on non-exudative dry AMD in the absence of direct measurements of the AMD[12].

Among the tetracycline derivatives, doxycycline is a possible candidate for long-term treatment of inflammation associated with atrophic AMD given a clear dosing split has been identified between its antimicrobial (>100 mg/day) and anti-inflammatory (40 mg/day) properties. Subantimicrobial doxycycline has found widespread clinical use for long-term suppression of acneiform and rosacea skin lesions with treatment effect dependent on its anti-inflammatory rather than anti-bacterial properties[12]. Subantimicrobial dose doxycycline has also found use in treating chronic periodontitis, proposed as a treatment for abdominal aneurysm, and as an adjunctive treatment in combination with methotrexate for rheumatoid arthritis[19-21].

Unfortunately, there exists plentiful data within the literature that seriously calls this conclusion into question regarding doxycycline's efficacy, and suggests low-dose, subantimicrobial is in-fact unlikely to be effective for treatment of non-exudative AMD, retinopathy from any cause, or CNS disease in general. While doxycycline is effective in murine models of laser induced AMD this model involves an acute insult that disrupts the blood brain barrier as a result of the injury, allowing direct access of doxycycline to the retina. This observation is important given the significantly lower penetration of the blood brain barrier by doxycycline as compared to other tetracycline derivatives. Minocycline attains levels in the brain nearly 3-fold higher than doxycycline at the same dose[20]. This finding may help explain why in a randomized, placebo-controlled trial using doxycycline 200 mg and rifampin 300 mg orally daily there were no beneficial effects on cognition or functioning in early dementia patients when doxycycline was used alone or in combination with rifampin[22] Similarly, multiple randomized controlled trials have failed to show an effect of statins on Alzheimer's disease despite predictions it is mechanistically involved in progression of disease, and this is thought to also be due in part to the limited ability for statins to cross the blood brain barrier[23]. Finally, in the only human trial for treatment of retinal disease using submicrobial doxycycline, ORACEA®, a sustained release subantimicrobial dose of doxycycline, demonstrated essentially no efficacy at preventing the progression of diabetic retinopathy[24]. There was no similar effect on central macular thickness with ORACEA® as indicated by prior limited studies using minocycline[18]. Thus, prior to the instant disclosure, the potential applicability of doxycycline, antimicrobial or submicrobial dose, for treatment of non-exudative AMD remained, at best, speculative and unproven.

Despite the equivocal data regarding submicrobial doxycycline for treatment of central nervous system (CNS) and retinal disease, there is ample evidence to suggest it can impact systemic, non-CNS disease. ORACEA® is a tetracycline derivative that is approved for treatment of inflammatory lesions of rosacea in adults[25, 26]. Notably, treatment of rosacea or ocular rosacea does not require the drug to cross the blood brain barrier. Rosacea is a chronic inflammatory disorder with characteristic skin lesions that include redness, visible blood vessels, papules and pustules that appear on the forehead, nose, and cheeks. ORACEA® tetracycline derivative contains 30 mg immediate release and 10 mg delayed release beads of doxycycline. The presumed mechanism of action is through reduction of skin inflammation rather than antimicrobial properties, as 40 mg doxycycline is known to be a subantimicrobial dose[26].

Del Rosso et al. compared ORACEA® tetracyclie derivative versus placebo for treatment of rosacea in two (study 301 and 302) phase III, placebo controlled, double blind, randomized multicenter studies[25]. In Study 301, 32% of the subjects were 51 to 70 years of age and 33% in Study 302. In both studies, participants received ORACEA® tetracycline derivative (n=269) or placebo (n=268) once daily for 16 weeks. The mean number of inflammatory lesions at baseline was approximately 20 in both studies. By week 16, study 301 showed a decrease in inflammatory lesions of −11.8 in the treatment versus −9.5 in control groups. In comparison, study 302 showed a decrease of −5.9 compared to −4.3 in treatment versus control group ($p<0.001$ for both studies).

In both study 301 and 302, ORACEA® tetracycline derivative was well-tolerated, with no major safety issues identified in the treatment group. For study 301, adverse events were reported in 44% of treatment versus 38.7% of control group participants, with most adverse events rated as mild or moderate in severity. Common adverse events included: diarrhea (4.8% treatment versus 3.3% control), nasopharyngitis (4.4% treatment versus 2.6% control), and headache (4.4% treatment versus 5.9% control). All subjects received hematology and serum chemistry panels at baseline and week 16 with no significant deviations or trends identified during the course of treatment.

A randomized, double-blind, placebo-controlled parallel group study evaluated the efficacy of adjunctive ORACEA® tetracycline derivative (Galderma Laboratories, L.P., Fort Worth, Texas, United Sates of America) compared to placebo in adult subjects with untreated periodontitis. Subjects were treated by scaling and root planning (SRP) and were assigned to receive either ORACEA® tetracycline derivative or placebo once daily for 9 months. The study demonstrated ORACEA® tetracycline derivative as an adjunct to SRP achieved significantly greater clinical benefits compared to SRP alone[27]. Again, treatment of periodontitis does not require transit of ORACEA® tetracycline derivative thru the blood brain barrier.

With respect to microbiologic outcomes, the study demonstrates that long-term use of ORACEA® tetracycline derivative does not result in a change in microbial flora, an increase in doxycycline resistance, the acquisition of doxycycline resistance, or the emergence of cross-resistance or multi-antibiotic resistance[27].

Longer term systemic interventions with subantimicrobial dose doxycycline have also been examined. A double-blind, placebo-controlled trial that evaluated the intestinal flora in adult subjects with chronic periodontitis demonstrated long-term treatment with subantimicrobial dose doxycycline has no antibacterial effect on intestinal flora. 69 subjects (30-75 years of age) were randomized to receive either 20 mg doxycycline (subantimicrobial dose) or placebo-control twice-daily for 9 months. Specifically, the results suggest a 9-month regimen of subantimicrobial dose doxycycline does not result in: a change in the normal fecal or vaginal flora, an increase in doxycycline resistance, the acquisition of doxycycline resistance, or the emergence of multi-antibiotic resistance[28]

Four multicenter, placebo-controlled, double-blind, randomized clinical trials evaluated the administration of multiple doses of subantimicrobial dose doxycycline for the treatment of adult periodontitis. In studies 1-3, 437 subjects were randomized to receive placebo, 10 mg doxycycline daily, 20 mg doxycycline daily, or 20 mg doxycycline twice daily for 12 months. In study 4, 190 subjects were randomized to either placebo or 20 mg doxycycline twice daily for 9 months. A meta-analysis of all four studies showed doxycycline was well-tolerated and reported adverse events were similar between the doxycycline groups and placebo control group with no difference in the occurrence of adverse reactions usually associated with higher-dose tetracyclines between the groups[29]. No clinically significant differences were identified for liver or kidney function tests in the treatment groups as compared to the control group and no resistance developed to doxycycline during the course of the study[29].

A randomized, double-blind clinical study compared the efficacy of doxycycline adjunctive to methotrexate (MTX) versus MTX alone in 66 adult subjects (27-74 years of age) with early seropositive rheumatoid arthritis (RA). Subjects were randomized to: 100 mg doxycycline (antimicrobial dose) twice-daily plus MTX, 20 mg doxycycline (subantimicrobial dose) twice-daily plus MTX, or placebo plus MTX for a period of two years. Both doxycycline treatment groups exhibited the same reduction in RA severity over the course of the study, and the improvement in both treatment groups was greater than the improvement exhibited by the placebo-control group[21]. Additionally, the number of adverse events by the placebo-control group reported in the subantimicrobial dose treatment group and the placebo group was equivalent and less than the number of adverse events reported by the antimicrobial dose treatment group[21].

A two year, double-masked, randomized trial compared treatment with 20 mg doxycycline (subantimicrobial dose) twice daily versus placebo in 128 post-menopausal women 45-70 years age (at the time of screening) with chronic periodontitis. Results showed a statistically significant reduction in serum inflammatory biomarkers hs-CRP and MMP-9 in the treatment versus control group. Notably, there was no sign of microbiological resistance in the treatment group as compared to the placebo group and no significant safety issues were identified during the course of the study[20].

As disclosed herein, submicrobial doxycycline would potentially offer substantial benefits over minocycline if it was proven efficacious for non-exudative AMD. First, there is no known dosing split between the anti-microbial properties and anti-inflammatory properties of minocycline.

Thus, there is the potential for inducing microbial resistance with long term use of minocycline as required for treating a chronic disease such as non-exudative AMID[30]. Second, minocycline has a significantly greater profile of adverse effects including hypersensitivity reactions, and a potentially lethal lupus-like syndrome[30].

Moreover, in addition to these well-known benefits, it is proposed in accordance with the presently disclosed subject matter that submicrobial dose doxycycline (40 mg) may surprisingly in of itself demonstrate greater efficacy than either higher dose anti-microbial doses of doxycycline (100 mg) or minocycline for treating non-exudative AMD. This result would not be anticipated or expected based on prior literature examining the ocular effects of tetracycline derivatives. Instead, prior to the instant disclosure, it would have been expected that either submicrobial doxycycline would not work at all due to issues passing thru the blood brain barrier, or that if anything a higher dose of doxycycline would achieve higher tissue levels in the retina and thus have greater efficacy for treating non-exudative AMD. it is proposed in accordance with the presently disclosed subject matter that there is in fact synergistic effect of submicrobial doxycycline on the microbiome as well as its previously known effects on multiple systemic anti-inflammatory pathways and its inhibition of microglial activity. It is further proposed in accordance with the presently disclosed subject matter that in some embodiments it is the combination of these two treatment effects that can achieve maximum efficacy for preventing progression of non-exudative AMD[31]. High dose doxycycline and minocycline would not be expected to achieve similar efficacy for non-exudative AMD due to their anti-microbial effects. These anti-microbial effects would be expected to dramatically alter the gut flora, causing a shift towards populations of bacteria not susceptible to doxycycline/minocycline. The altered composition of the gut microbiome due to these anti-microbials is likely to cause gut leakage that worsens macular degeneration.[31]

In contrast, it is proposed in accordance with the presently disclosed subject matter that submicrobial doxycycline impacts non-exudative AMD by several independent pathways. First, without being bound by any particular theory or mechanism of action, submicrobial doxycycline should be able to decrease gut leakage of multiple inflammatory cytokines and prevent activation of inflammatory cells that can transit to the retina. The gut microflora retains the same composition, but the doxycycline lowers their inflammatory potential. Moreover, without being bound by any particular theory or mechanism of action, submicrobial doxycycline furthers inhibit activation of microgial in the retina after the drug transits to the eye. Submicrobial doxycycline is finally able to inhibit multiple pro-inflammatory pathways in the eye including MMPs, cytokines, reactive oxygen species as previously described for this medication. It is proposed in accordance with the presently disclosed subject matter that it is specifically the calming of the gut microflora that independently affects progression of dry AMD, separate from its systemic anti-inflammatory effects. High dose doxycycline would be expected to rather than calm, actually kill gut bacteria, altering the microbiome profile to one more likely to precipitate progression of dry AMD, and thus counteracting any anti-inflammatory effects in the eye itself. Minocyclines effects are expected to be intermediate due to greater blood brain barrier penetration, allowing more direct inhibition of microglia and inflammation in the eye, but with the negative impact on the gut microflora microbiome due to its anti-bacterial activity.

Additionally, the present disclosure indicates that the efficacy of tetracycline or its derivatives can be directly predicted from the structure of the molecule. The dimethylamino group at the C4 carbon on the upper half of the molecule is necessary for antimicrobial activity. 4-de-dimethylamino tetracyclines, also called chemically modified tetracyclines (CMTs), lack antimicrobial activity in vivo presumably due to the inability of the molecule to adapt a zwitterionic form necessary for activity. Based on aspects of the instant disclosure, an ideal tetracycline derivative for treatment of non-exudative AMD will either be given at a sufficiently low dose that is non-antimicrobial, or will lack the dimethylamino group entirely, preventing microbial activity.

Further, in some embodiments, the ideal tetracycline derivative for treatment of non-exudative macular degeneration may retain the lower half of the molecule as it can in some aspects be necessary for binding to both prokaryotic and eukaryotic targets, which can in some embodiments be necessary for effectiveness of the drug. This region can allow for metal ion chelation necessary for its activity against matrix metalloproteinases. In particular, in some embodiments, an ideal tetracycline derivative for non-exudative AMD can have increased affinity for Zn2+ to increase MMP inhibitory activity. The ideal tetracycline derivative can also have a structure allowing enhanced lipophilicity to allow greater penetration of the blood brain barrier for transport to the retina and penetration of gram-positive bacteria, but at concentrations that within the gram-positive bacteria do not permit inhibition of protein synthesis.

Finally, in some embodiments, an ideal tetracycline derivative for treatment of non-exudative AMD can have a phenol ring, as the presence of a phenol ring can allow for scavenging of reactive oxygen species. Ideally, the tetracycline derivative can have a diethyamino group on the phenolic carbon to allow for improved scavenging capability, in some applications. As discovered and disclosed herein, one such candidate is doxycycline given at a dose of 40 mg per day, but not at its usual dose of 100 mg per day. At 40 mg per day doxycycline does not have anti-microbial activity as it is below the minimum inhibitory concentration for the molecule. In another embodiment doxycycline can be given as a sustain release molecule. In one particular embodiment this sustained release molecule is ORACEA® tetracycline derivative, consisting of 30 mg immediate release doxycycline and 10 mg sustained release doxycycline.

EXAMPLES

The following examples are included to further illustrate various embodiments of the presently disclosed subject matter. However, those of ordinary skill in the art should, in light of the present disclosure, appreciate that many changes can be made in the specific embodiments which are disclosed and still obtain a like or similar result without departing from the spirit and scope of the presently disclosed subject matter.

Example 1

Studies were conducted to assess doxycycline given at a dose of 40 mg per day, but not at its usual dose of 100 mg per day. At 40 mg per day doxycycline is shown to have no anti-microbial activity as it is below the minimum inhibitory concentration for the molecule. In some embodiments, doxycycline can be given as a sustain release molecule.

Additionally, in some embodiments this sustained release molecule is ORACEA® tetracycline derivative, consisting of 30 mg immediate release doxycycline and 10 mg sustained release doxycycline.

Figure 4:
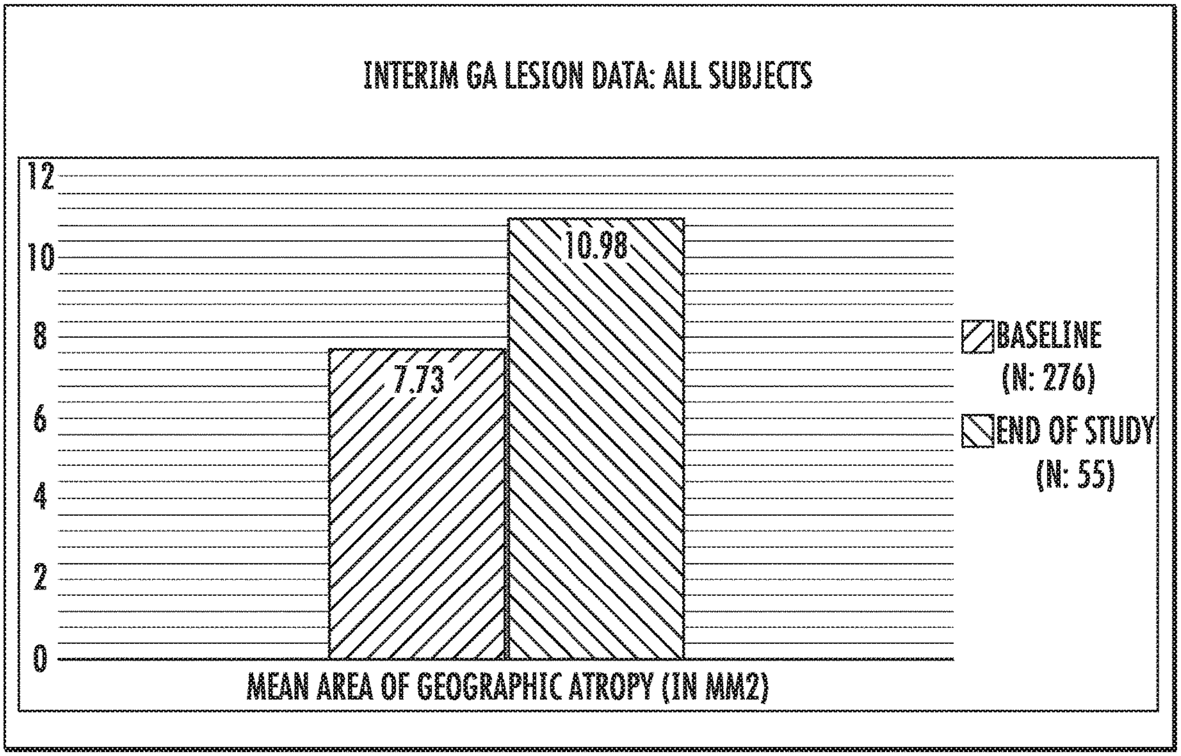
FIG. 4 shows the results of submicrobial doxycycline on non-exudative age related macular degeneration based on the progression of the established geographic atrophy lesions, as measured by growth in the overall area of atrophy during a 24 month period.

More particularly, a study was conducted to verify efficacy of submicrobial doxycycline against non-exudative macular degeneration, also referred to as the TOGA study (Treatment with ORACEA® tetracycline derivative for geographic atrophy). In contrast to prior assertions of efficacy of tetracyclines against macular degeneration, this study was specifically designed to measure the gold standard progression of geographic atrophy as the metric for efficacy of the medication against this disease. In the TOGA study patients were assigned to either placebo or ORACEA® tetracycline derivative once a day for 24 months. Endpoints were the progression of the established geographic atrophy lesions, as measured by growth in the overall area of atrophy during the 24 month period. Expected growth was normalized against starting lesion size of the area of geographic atrophy. Normative date from the age related eye disease study indicates an expected growth rate of 2.2 $mm^2$ per year per natural history of the disease. 286 patients were enrolled in the study. With an average patient starting lesion size for the geographic atrophy of 7.73 $mm^2$, the expected average lesion size over the 24 month study from the natural history of the disease would be 12.13 $mm^2$ for all corners. However, an average lesion size of 10.98 $mm^2$ was measured indicating a reduction in expected lesion growth of 1.15 $mm^2$, or 26%, as shown in FIG. 4. With the understanding that half of the patients are on placebo and half on ORACEA® tetracycline derivative this would translate to a likely 52% reduction in the expected rate of growth of the area of geographic atrophy in patients taking ORACEA® tetracycline derivative as compared to placebo pill.

These results are the first to demonstrate a direct effect of submicrobial doxycycline on non-exudative age related macular degeneration. These results are unexpected given the established previously demonstrated low penetration of the blood brain barrier by doxycycline in general, the likely low tissue concentration of doxycycline in the retina given the use of a 40 mg low dose, the lack of significant efficacy for ORACEA® tetracycline derivative treatment of diabetic retinopathy, and perhaps most importantly the lack of any therapeutic thus far to demonstrate established efficacy for treatment of this disease.

Example 2

Figure 5A:
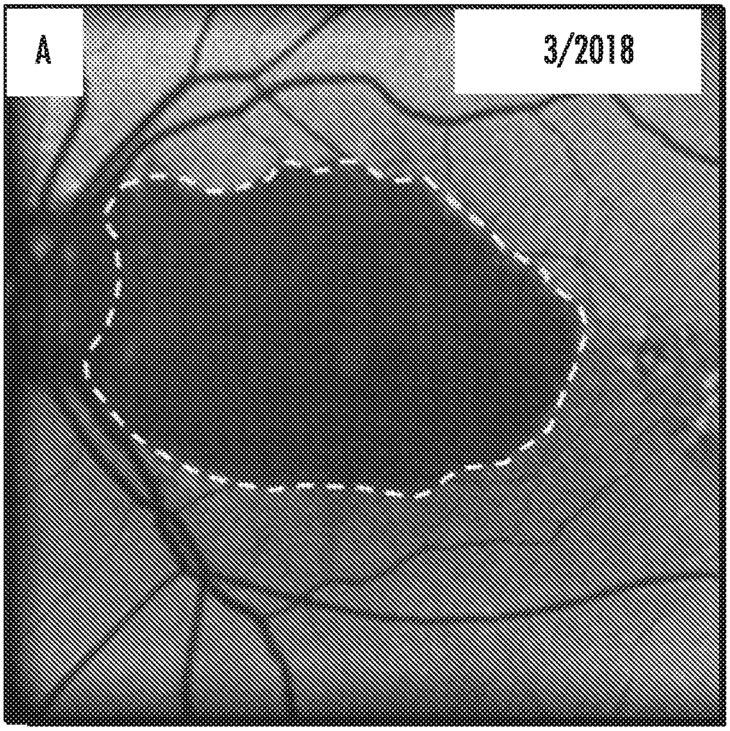
FIGS. 5A-5H show images of geographic atrophy lesions in the eye from patients receiving a 40 mg/day dose of doxycycline (a non-antimicrobial dose as disclosed herein) for one to two years.
Figure 5B:
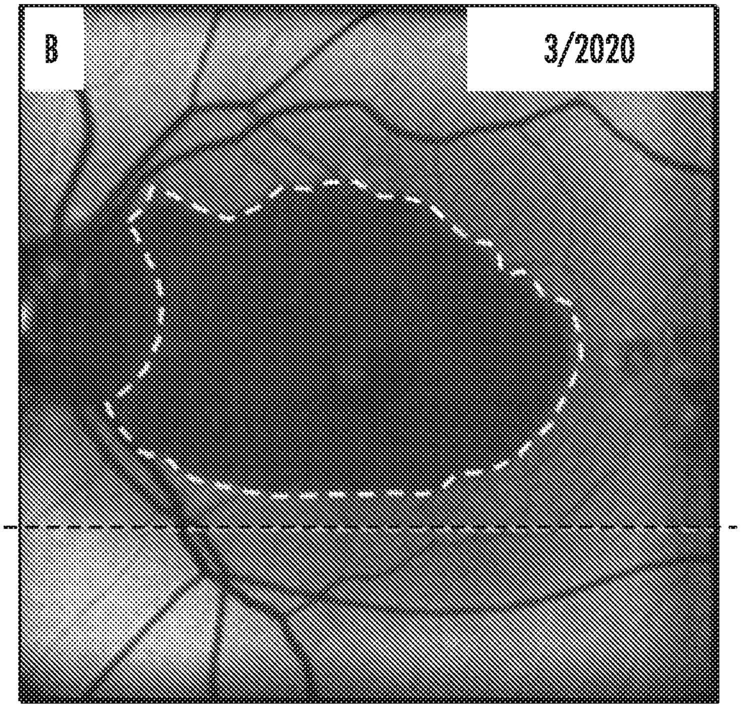
Figure 5C:
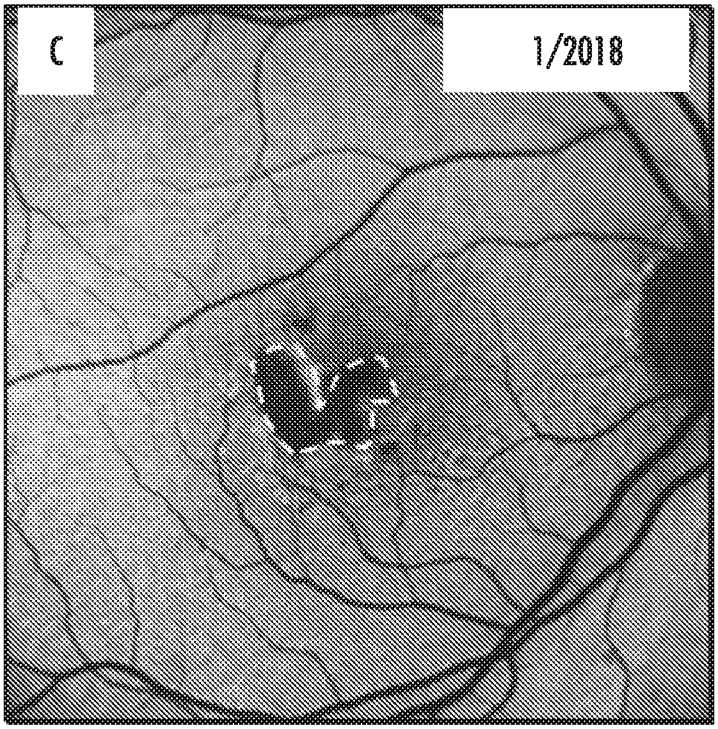
Figure 5D:
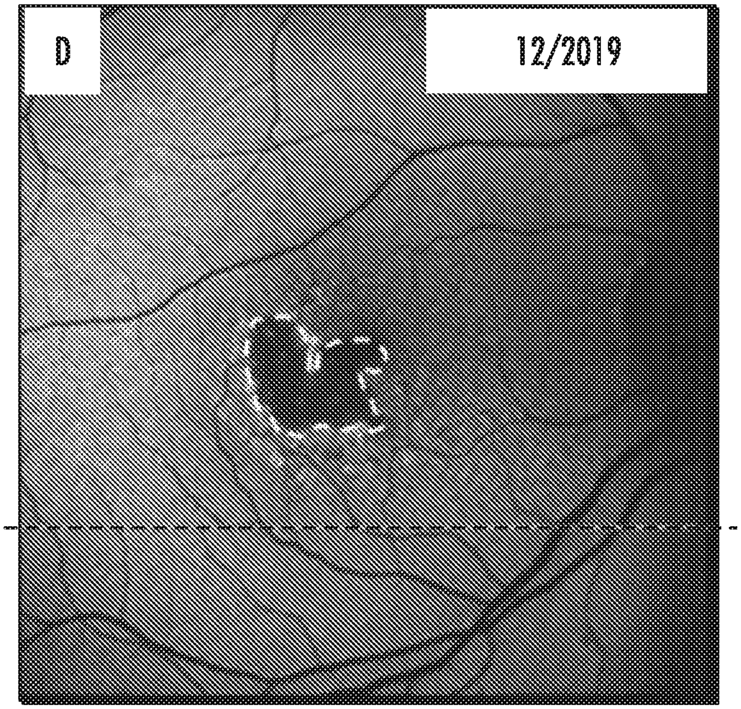
Figure 5E:
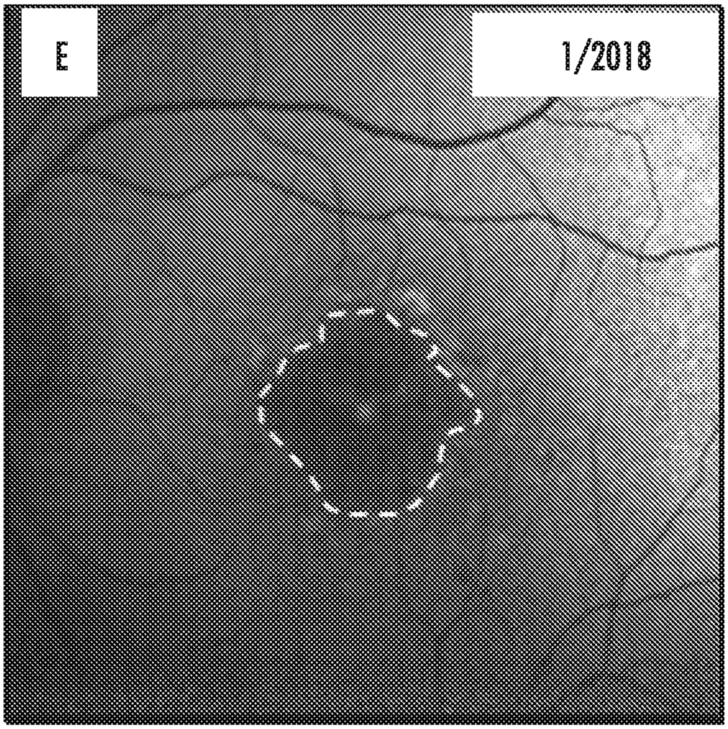
Figure 5F:
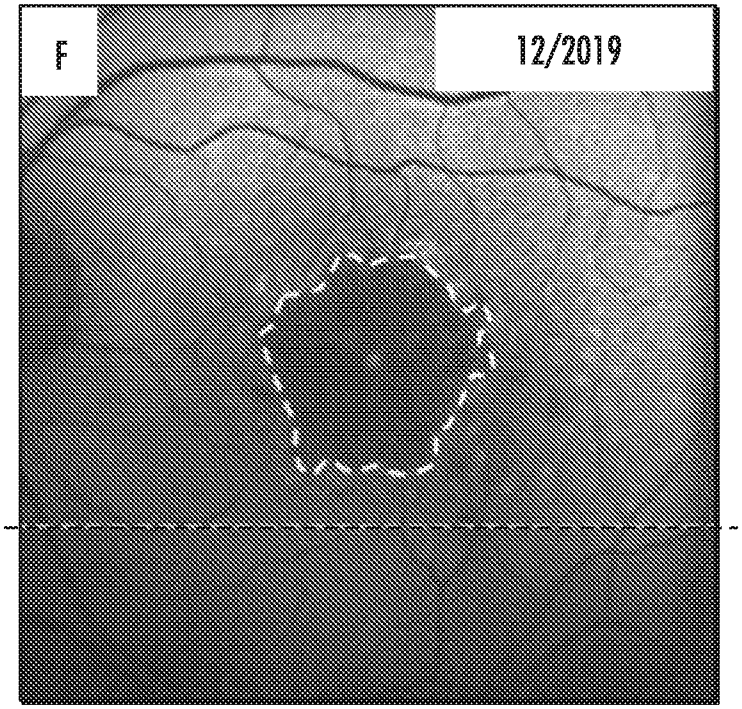
Figure 5G:
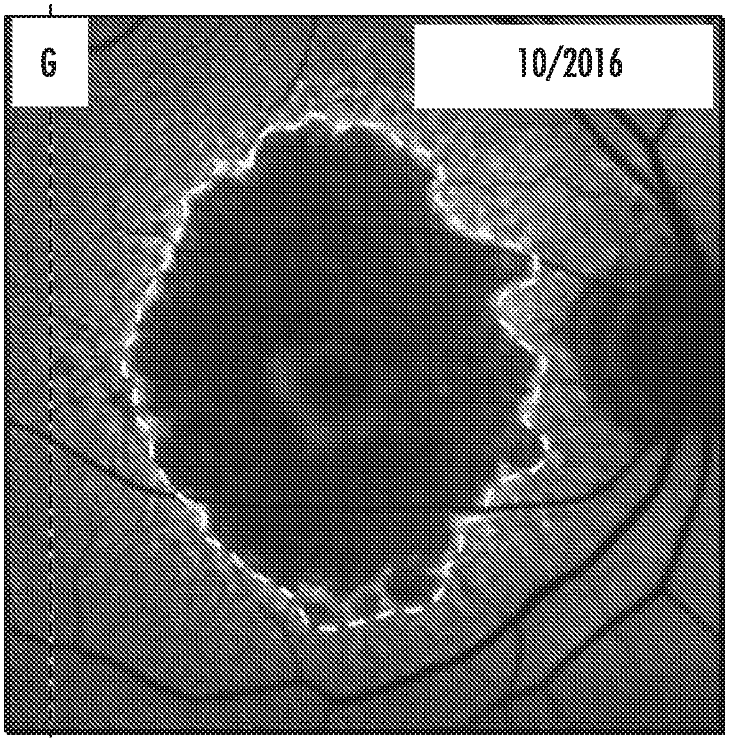
Figure 5H:
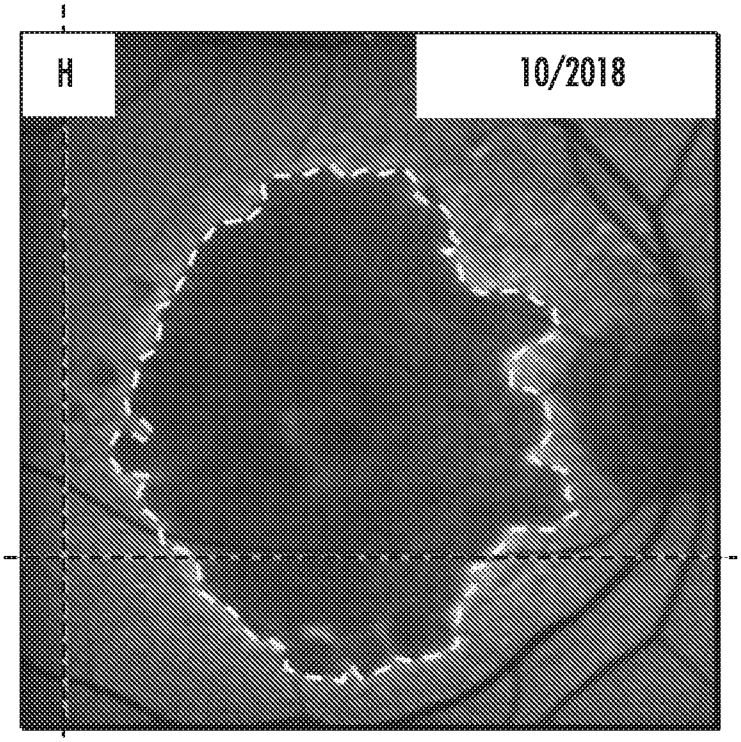

Further studies were conducted to assess doxycycline given at a dose of 40 mg per day and its affects on two-year growth rates of geographic atrophy lesions. The measurements were taken from patients receiving a 40 mg/day dose of doxycycline (a non-antimicrobial dose as disclosed herein). FIGS. 5A-5H show images of geographic atrophy lesions from representative patients in the study taken one to two years apart (FIGS. 5A-5B, Patient 1; FIGS. 5C-5D, Patient 2; FIGS. 5E-5F, Patient 3; FIGS. 5G-5H, Patient 4). Geographic atrophy lesions increased in size, and expansion was greater for lesions that are larger to begin with. However, all lesions expanded more slowly than would be anticipated based on previously published studies of the natural rate of expansion of geographic atrophy lesion based on starting lesion size.

This data further demonstrates the effectiveness of administering a non-antimicrobial dose of doxycycline or its derivatives to a patient suffering from AMD to reduce and/or slow the progression of geographic atrophy lesions in the eye.

Discussion of Examples

The data presented herein supports an approach that:

1) places intestinal bacteria in a kind of suspended animation. That is, without being bound by any particular theory, doxycycline is relatively broad spectrum and at low doses may interfere with protein synthesis just enough to keep them around and not get replaced by unwanted bacertia, but effectively guts their worst tendencies; and 2) calms and quiets the anti-inflammatory profile of intestinal bacteria that gives rise to significant stimulated anti-inflammatory cells and calms those activated inflammatory cells as well in the gut and at distant sites, e.g., microglia in eye.

That is to say the presently disclosed compositions are configured to bind to ribosomes to inhibit protein synthesis at a level that quiets but does not kill intestinal bacterial, and also alters the inflammatory profile by inhibiting one or more of the following pathways: MMP, caspase, ROS, cytokines, etc. Thus, in some embodiments, the disclosed compositions, particularly for purposes of treating AMD, 1) should preferably be configured for oral administration in order to reach the microbiome of a subject to which it is administered; 2) preferably be configured to affect bacteria, while also being non anti-microbial to allow the secretome of the microbiome that is now present to be calmed down to be consistent and not change to an even worse microbial assortment; and 3) preferably have the ability to inhibit one or more inflammatory pathways both within the affected microbiome and in inflammatory cells in the affected tissues where inflammation is occurring.

As the data herein demonstrate, one potential example compound that achieves these desired characteristics and has these properties is a low dose doxycycline. However, the data herein support the use of any tetracycline that has one, some or all of the following properties:

1) comprises a four ring core;
2) comprises a dimethylamino group at the C4 carbon to allow binding to one or more of 30 s and 50 s sites on bacterial ribosomes;
3) is suitable for administration at a concentration that is below the minimum inhibitory concentration so that protein synthesis inhibition is not lethal to bacteria;
4) includes a chemical structure suitable for chelation of Zn', optionally at least the lower half of the molecule structure which is configured for chelation of $Zn^{2+}$;
5) is suitable for administration at a concentration necessary to bind sufficient $Zn^{2+}$ to inhibit MMP at the same concentration that affects protein inhibition in bacteria to place them in suspended animation;
6) is capable, at or near the concentration in 5) above, to reach sufficient tissue levels in ocular tissues so as to accumulate intracellular to inhibit ocular microglia activation; and/or
7) is suitable for treating macular degeneration.

As noted above, examples of such molecules are ORACEA® tetracycline derivative, or doxycycline, administered at a dose of about 40 mg per day, or less. Unexpectedly, it was found that an effective compound for treating AMD is one that retains its anti-microbial protein synthesis inhibiting activity but at a level of inhibition that is not actually anti-microbial. The presumption would have been that if one went below 40 mg a day that it would lose efficacy against inflammation because of inability to do all those inflammatory things that come from the bottom half of the molecule. However, the data herein indicate otherwise, and show that what may be needed is to inhibit protein synthesis in these bacteria, which is needed to prevent inflammatory activation of end effector macrophages and neutrophils that then travel to distant sites. Yet, the compound and dosage should ideally be such that the bacteria in the microbiome are not actually killed, or at least there is minimal impact on the microbiome, because then they would be replaced with other bad or less preferred bacteria. This is a new mechanism for anti-inflammatory properties of tetracyclines.

REFERENCES

All references listed herein including but not limited to all patents, patent applications and publications thereof, scientific journal articles, and database entries (e.g., GENBANK® database entries and all annotations available therein) are incorporated herein by reference in their entireties to the extent that they supplement, explain, provide a background for, or teach methodology, techniques, and/or compositions employed herein.

1. Available from: http://www.who.int/mediacentre/factsheets/fs282/en/.
2. Wirostko, E., W. Wirostko, and B. Wirostko, *Age related macular degeneration is an inflammatory disease possibly treatable with minocycline*. Acta Ophthalmol, 2004. 82(2): p. 243-4.
3. Wirostko, E., U.S. Pat. No. 6,218,368. 1999.
4. Ting, A. Y., T. K. Lee, and I. M. MacDonald, *Genetics of age-related macular degeneration*. Curr Opin Ophthalmol, 2009. 20(5): p. 369-76.
5. Antoniak, K., W. Bienias, and J. Z. Nowak, [*Age-related macular degeneration—a complex genetic disease*]. Klin Oczna, 2008. 110(4-6): p. 211-8.
6. Anderson, D. H., et al., *Characterization of beta amyloid assemblies in drusen: the deposits associated with aging and age-related macular degeneration*. Exp Eye Res, 2004. 78(2): p. 243-56.
7. Ramrattan, R. S., et al., *Morphometric analysis of Bruch's membrane, the choriocapillaris, and the choroid in aging*. Invest Ophthalmol Vis Sci, 1994. 35(6): p. 2857-64.
8. Gehrs, K. M., et al., *Age-related macular degeneration—emerging pathogenetic and therapeutic concepts*. Ann Med, 2006. 38(7): p. 450-71.
9. Brown, M. M., et al., *Age-related macular degeneration: economic burden and value-based medicine analysis*. Can J Ophthalmol, 2005. 40(3): p. 277-87.
10. Donoso, L. A., T. Vrabec, and H. Kuivaniemi, *The role of complement Factor H in age-related macular degeneration: a review*. Surv Ophthalmol, 2010. 55(3): p. 227-46.
11. Soliman, G. M., et al., *Minocycline block copolymer micelles and their anti-inflammatory effects on microglia*. Macromol Biosci, 2010. 10(3): p. 278-88.
12. Alikhan, A., L. Kurek, and S. R. Feldman, *The role of tetracyclines in rosacea*. Am J Clin Dermatol, 2010. 11(2): p. 79-87.
13. Cox, C. A., et al., *Doxycycline's effect on ocular angiogenesis: an in vivo analysis*. Ophthalmology, 2010. 117 (9): p. 1782-91.
14. Zhao, L., et al., *Minocycline attenuates photoreceptor degeneration in a mouse model of subretinal hemorrhage microglial: inhibition as a potential therapeutic strategy*. Am J Pathol, 2011. 179(3): p. 1265-77.
15. Scholz, R., et al., *Minocycline counter-regulates pro-inflammatory microglia responses in the retina and protects from degeneration*. J Neuroinflammation, 2015. 12: p. 209.
16. Leung, D. W., et al., *Minocycline protects photoreceptors from light and oxidative stress in primary bovine retinal cell culture*. Invest Ophthalmol Vis Sci, 2007. 48(1): p. 412-21.
17. Sivaprasad, S., et al., *A pilot study on the combination treatment of reduced-fluence photodynamic therapy, intravitreal ranibizumab, intravitreal dexamethasone and oral minocycline for neovascular age-related macular degeneration*. Ophthalmologica, 2011. 225(4): p. 200-6.
18. Cukras, C. A., et al., *Oral minocycline for the treatment of diabetic macular edema (DME): results of a phase I/II clinical study*. Invest Ophthalmol Vis Sci, 2012. 53(7): p. 3865-74.
19. Lindeman, J. H., et al., *Clinical trial of doxycycline for matrix metalloproteinase-9 inhibition in patients with an abdominal aneurysm: doxycycline selectively depletes aortic wall neutrophils and cytotoxic T cells*. Circulation, 2009. 119(16): p. 2209-16.
20. Payne, J. B., et al., *The effect of subantimicrobial-dose-doxycycline periodontal therapy on serum biomarkers of systemic inflammation: a randomized, double-masked, placebo-controlled clinical trial*. J Am Dent Assoc, 2011. 142(3): p. 262-73.
21. O'Dell, J. R., et al., *Treatment of early seropositive rheumatoid arthritis: doxycycline plus methotrexate versus methotrexate alone*. Arthritis Rheum, 2006. 54(2): p. 621-7.
22. Molloy, D. W., et al., *A multicenter, blinded, randomized, factorial controlled trial of doxycycline and rifampin for treatment of Alzheimer's disease: the DARAD trial*. Int J Geriatr Psychiatry, 2013. 28(5): p. 463-70.
23. McGuinness, B., et al., *Cochrane review on 'Statins for the treatment of dementia'*. Int J Geriatr Psychiatry, 2013. 28(2): p. 119-26.
24. Scott, I. U., et al., *Effect of doxycycline vs placebo on retinal function and diabetic retinopathy progression in mild to moderate nonproliferative diabetic retinopathy: a randomized proof-of-concept clinical trial*. JAMA Ophthalmol, 2014. 132(9): p. 1137-42.
25. Del Rosso, J. Q., et al., *Two randomized phase III clinical trials evaluating anti-inflammatory dose doxycycline (40-mg doxycycline, USP capsules) administered once daily for treatment of rosacea*. J Am Acad Dermatol, 2007. 56(5): p. 791-802.
26. Del Rosso, J. Q., *The ORCA (Oracea for rosacea: a community-based assessment) trial: a large-scale, phase 4 trial in papulopustular rosacea*. Cutis, 2010. 86(5 Suppl): p. 4-6.
27. Preshaw, P. M., et al., *Modified-release subantimicrobial dose doxycycline enhances scaling and root planing in subjects with periodontal disease*. J Periodontol, 2008. 79(3): p. 440-52.
28. Walker, C., et al., *Long-term treatment with sub-antimicrobial dose doxycycline has no antibacterial effect on intestinal flora*. J Clin Periodontol, 2005. 32(11): p. 1163-9.
29. Ciancio, S. and R. Ashley, *Safety and efficacy of sub-antimicrobial-dose doxycycline therapy in patients with adult periodontitis*. Adv Dent Res, 1998. 12(2): p. 27-31.
30. Kircik, L. H., *Doxycycline and minocycline for the management of acne: a review of efficacy and safety with emphasis on clinical implications*. J Drugs Dermatol, 2010. 9(11): p. 1407-11.

31. Rinninella, E., et al., *The Role of Diet, Micronutrients and the Gut Microbiota in Age-Related Macular Degeneration: New Perspectives from the Gut(–)Retina Axis*. Nutrients, 2018. 10(11).

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A method of treating non-exudative age-related macular degeneration (AMD) in a subject, the method comprising:

providing a subject susceptible to and/or suffering from non-exudative AMD; and administering doxycycline to the subject, wherein the doxycycline is administered at a dose of about 100 mg per day, at a dose of about 40 mg per day, or at a dose of less than about 40 mg per day.

2. The method of claim 1, wherein the doxycycline is administered at a dose of less than about 40 mg per day.

3. The method of claim 1, wherein the dose of the doxycycline is sufficient to inhibit activation of gut microbiome inflammatory cells.

4. The method of claim 1, wherein the dose of the doxycycline is sufficient to decrease gut leakage of inflammatory cytokines.

5. The method of claim 1, wherein the dose of the doxycycline is below a minimum inhibitory concentration for antimicrobial activity.

6. The method of claim 1, wherein the dose of the doxycycline is sufficient to prevent activation of inflammatory cells that can transit to a retina of the subject.

7. The method of claim 1, wherein the dose of the doxycycline is sufficient to inhibit pro-inflammatory pathways to an eye of the subject.

* * * * *